United States Patent [19]

Bailey et al.

[11] Patent Number: 5,440,045
[45] Date of Patent: Aug. 8, 1995

[54] TRIAZOLINONE RING FORMATION IN TERT-BUTANOL

[75] Inventors: Allan R. Bailey, St. Louis, Mo.; Marc Halfon, Cranbury; Eric W. Sortore, Trenton, both of N.J.

[73] Assignee: FMC Corporation, Philadelphia, Pa.

[21] Appl. No.: 365,977

[22] Filed: Dec. 28, 1994

Related U.S. Application Data

[60] Division of Ser. No. 117,473, Sep. 7, 1993, abandoned, which is a continuation-in-part of Ser. No. 882,653, May 13, 1991, Pat. No. 5,256,793.

[51] Int. Cl.⁶ .............................................. C07D 249/12
[52] U.S. Cl. ................................ 548/263.2; 564/251
[58] Field of Search ...................... 548/263.2; 564/251

[56] References Cited

U.S. PATENT DOCUMENTS 4,980,480  12/1990  Theordoridis ................. 548/263.2

FOREIGN PATENT DOCUMENTS 60-136572A  7/1985  Japan .
60-136573A  7/1985  Japan .
63-093768   4/1988  Japan .
2021586     5/1978  United Kingdom .

OTHER PUBLICATIONS

Research Disclosure, 27805, p. 358, Jun. 1987.
Bulletin of the Chemical Society of Japan—Tsuge—47(11) 2676 (1974).

*Primary Examiner*—Richard L. Raymond
*Attorney, Agent, or Firm*—H. Robinson Ertelt; Robert M. Kennedy; Norman L. Craig

[57] ABSTRACT

A process for the production of an aryl triazolinones of the formula

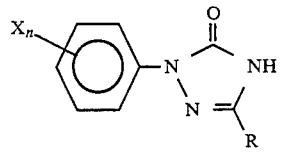

wherein

R is lower alkyl and:

$X_n$ is 2,4-dichloro-5-methylsulfonylamino; 2-chloro-5-methylsulfonylamino; 4-chloro-5-methylsulfonylamino; 3-methylsulfonylamino; 4-chloro; 2-chloro; 3-nitro; 4-chloro-3-nitro; 2-chloro-5-nitro; 2,4-dichloro-5-nitro; 2-fluoro; 2-4-chloro; 2,4-dichloro; 4-alkoxy; or 4-alkoxy-2-fluoro;

which comprises treating, in a tert-butanol medium, an aryl hydrazine of the formula

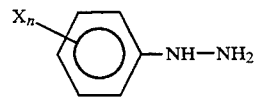

sequentially with (i) a $C_1$–$C_3$ aldehyde, (ii) a cyanate and weak organic acid, and (iii) a hypohalous acid, a salt thereof, or a halogen.

11 Claims, No Drawings

TRIAZOLINONE RING FORMATION IN TERT-BUTANOL

This application is a division of application Ser. No. 117,473, filed Sep. 7, 1993, now abandoned, which is a continuation-in-part of application Ser. No. 882,653, filed 13 May 1992, now U.S. Pat. No. 5,256,793.

This invention relates to the production of 1-aryl-1,2,4-triazolin-5-ones in a medium of tert-butanol.

U.S. Pat. No. 4,980,480 discloses a process for producing 1-aryl-1,2,4-triazolin-5-ones by treating an aryl triazolidinone with a hypohalous acid, a salt thereof, or a halogen. The triazolidinone may be produced by reacting an appropriate aryl hydrazine with an aldehyde to give the corresponding hydrazone followed by treatment with an alkali metal cyanate to give the triazolidinone. A medium is preferred in which the triazolidinone is at least partially soluble. Acetic acid is said to be a very suitable medium.

In accordance with one aspect of applicant's invention, a 1-aryl-1,2,4-triazolidin-5-one is treated in a medium of tert-butanol with a hypohalous acid, a salt thereof, or a halogen to form the corresponding triazolinone. The reaction proceeds rapidly at relatively low temperatures to give high yields in short reaction times. In another aspect of the invention, the triazolidinone may be produced in high yields in a medium of tert-butanol by reacting an aryl hydrazone with an alkali metal cyanate. The aryl hydrazone may in turn be produced by the reaction of an aryl hydrazine with an aldehyde in a tert-butanol medium.

The tert-butanol medium may be anhydrous tert-butanol or preferably a mixture of tert-butanol and water.

By using a tert-butanol medium, high yields of triazolinone may be obtained. Of particular advantage, both high yields and high purity of triazolinone product may be obtained in large scale production (e.g. with 2 lb-mole of the aryl hydrazine starting material using a 500 gallon reactor). Starting with the aryl hydrazine or aryl hydrazone, sequential steps of the process may be conducted in a single reactor by sequentially adding the reactants without the need to isolate or purify the intermediate products. Without further purification, other than water washing, the large scale as well as bench scale triazolinone product may be isolated and used directly in subsequent reactions such as difluoromethylation of the N-4 nitrogen of the triazolinone ring, or chlorination of the benzene ring. Prior to the present process, the medium of choice was acetic acid/water (U.S. Pat. No. 4,980,480). In the development of large scale production procedures using an acetic acid/water medium, product results were found to be variable. Triazolinone yields and purity were considerably lower than could be obtained at bench scale production, and the formation of increased side reaction products routinely required that the triazolinone be further purified before it could be used in subsequent reactions.

The isolation of the triazolinone or triazolidinone product may be easily effected by distilling off the 88/12 (wt/wt) tert-butanol/water azeotrope (BP 80° C.) which can be recycled for use in subsequent production. The product may thereby be recovered without resorting to extraction with organic solvents or energy intensive solvent removal of large amounts of higher boiling solvents such as water (BP 100° C.) or acetic acid (BP 118° C.). The process of this invention therefore may require lower energy use, provide a purer and less costly product, and be suitable for large scale operations.

Generally, use of an alcohol-containing medium would not be desirable for the present process. Under conditions such as those used to oxidize the triazolidinone, alcohols may be oxidized to their hydroperoxides. The hydroperoxides of most alcohols which might commonly be used as a reaction medium may then decompose to give aldehydes or ketones. If recycled with the tert-butanol medium such aldehydes or ketones could compete in the formation of the hydrazone, thereby contaminating the reaction system with unwanted products. The tert-butanol hydroperoxide, however, having no alpha hydrogens may decompose to regenerate tert-butanol, thereby diminishing potential contamination. Additionally the hydroperoxides of alcohols having alpha hydrogens may exhibit instability, potentially resulting in explosive decompositions. Tert-butanol which forms more stable hydroperoxides diminishes this problem.

The compounds produced in the present process are intermediates in the production of herbicides such as those shown in U.S. Pat. No. 4,818,275, the entire disclosure of which is incorporated herein by reference, such as compound number 1 of Table 1 of that patent. Various starting materials, reaction sequences and intermediates useful for making herbicides including those of the U.S. Pat. No. 4,818,275 patent are illustrated in U.S. Pat. No. 4,980,480, the entire disclosure of which is incorporated herein by reference. The preparation of various hydrazine and hydrazone starting materials which are useful in the present process are illustrated in columns 3, 4 and 7, and Example 5 of the U.S. Pat. No. 4,980,480 patent.

One aspect of this invention may be described by the following schema:

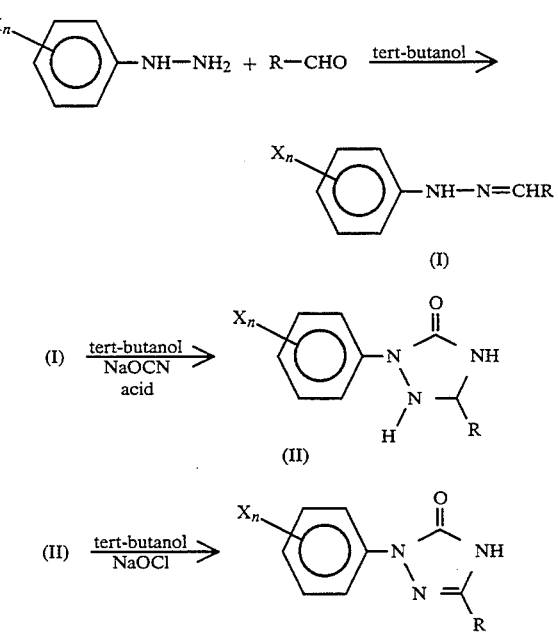

wherein:
R is lower alkyl;
X is independently halogen, lower alkyl, lower alkoxy, nitro, hydroxy, —NHSO₂R', —N(SO₂R')₂ or —N(R')SO₂R' where R' is lower alkyl, and n is a number from 0 to 3.

Preferred embodiments include those in which R is methyl, and $X_n$ is 2,4-dichloro-5-methylsulfonylamino; 2-chloro-5-methylsulfonylamino; 4-chloro-5-methylsulfonylamino; 3-methylsulfonylamino; 4-chloro; 2-chloro; 3-nitro; 4-chloro-3-nitro; 2-chloro-5-nitro; 2,4-dichloro-5-nitro; 2-fluoro; 2-fluoro-4-chloro; 2,4-dichloro; 4-alkoxy; or 4-alkoxy-2-fluoro. In a more preferred embodiment, R is methyl and the phenyl group is unsubstituted, that is n is 0.

In each aspect of the invention it is preferable that the substituted or unsubstituted alkyl radicals have fewer than seven carbon atoms.

As used herein, the term "lower" modifying "alkyl", "alkoxy" and the like implies a straight or branched hydrocarbon chain of 1–3 carbon atoms.

The term "halo" or "halogen" means fluorine, chlorine, or bromine.

The term "aryl" means phenyl or substituted phenyl.

The term "tert-butanol medium" refers to tert-butanol or tert-butanol/water mixtures in which the reactants and products of this process may be dissolved or dispersed. The terms "88/12", "95/5" and "70/30" used with tert-butanol/water, tert-butanol medium, tert-butanol azeotrope, and the like refer to the weight ratio of the tert-butanol/water mixture. Thus, the 88/12 azeotrope is 88 parts by weight of tert-butanol and 12 parts by weight of water.

In one aspect of the present invention an aliphatic aldehyde in a tert-butanol medium is reacted with an aryl hydrazine to produce the corresponding aryl hydrazone. The reaction may be carried out in a temperature range of −10° C. to 60° C. A temperature range of about 5° C. to 30° C. is preferred. The reactants may be used in equimolar concentrations or up to about twenty percent molar excess of the aldehyde. A one percent to ten percent molar excess of the aldehyde is preferred. The amount of tert-butanol medium used may be between 50 and 2000 grams of medium per mole of aryl hydrazine. The amount of tert-butanol medium used in any particular reaction system will vary depending on the particular reactants and the reaction conditions. The reactants may be individually dissolved in tert-butanol medium, and the aldehyde added to the aryl hydrazine. One preferred mode utilizes about 100 grams of tert-butanol medium/mole of aldehyde, and about 350 grams of tert-butanol medium/mole of phenylhydrazine.

In a second aspect of the present invention, an aryl hydrazone is reacted in a tert-butanol medium with an alkali metal cyanate and a proton source to form the aryl triazolidinone. This reaction may be carried out over a period of between one hour and 24 hours at a temperature of about −10° C. to 60° C. The reaction is preferably conducted over a period of about two hours to five hours at a temperature of about 0° C. to 35° C. Up to a 20% molar excess of cyanate may be used in this reaction. Preferably a 5% to 10% molar excess of cyanate is used. Suitable cyanates include sodium, potassium, and calcium cyanates, or a stable cyanate-delivering salt. Sodium cyanate is preferred. The proton source is preferably any simple, weak organic acid, for example, acetic acid, propionic acid, or butyric acid. Acetic acid is preferred. Up to about a 20% equivalent excess (based on sodium cyanate and its sodium carbonate impurity) of the acid may be used in the reaction. This amount of organic acid may be reduced, if old or poor quality aryl hydrazine was used in production of the aryl hydrazone, or unexpectedly poor yields of triazolinone are obtained. Organic acid in an amount equal to this reduction is instead added to the tert-butanol medium in the production of the aryl hydrazone. The amount of organic acid partitioned to hydrazone production may be up to about 50% (mole/mole) of the hydrazine starting material used. Preferably the organic acid is about 10% to 16% (mole/mole) of the hydrazine starting material. If the acid addition is partitioned, both hydrazone formation and triazolidinone formation reactions should be carried out in a temperature range of about 30° C. to 40° C.

Since the presence of acetic acid is believed to increase the amount of side reactions and polymerization, it is preferred that no more than 5% equivalent excess of acetic acid be used. Enough tert-butanol medium should be present to adequately solubilize the hydrazone. A preferred concentration would use about 400 gm of tert-butanol medium for each mole of hydrazone.

In a third aspect of the invention, an aryl triazolidinone is oxidized in a tert-butanol medium to give the desired aryl triazolinone. The reaction may be carried out at a temperature of about 0° C. to 60° C. Preferably the reaction is carried out over a period of between two hours to four hours at a temperature of about 10° C. to 40° C. The oxidation may be conducted using a halogen, a hypohalous acid, or a salt of the hypohalous acid. Sodium hypochlorite is the oxidant of choice. Aqueous solutions of sodium hypochlorite of about 5% to 25% (wt/wt) concentration may be used. Solutions of about 10% to 15% concentration are preferred. Up to about a 40% molar excess of sodium hypochlorite may be used. Molar excesses of up to about 10% are preferred.

Upon completion of the reaction, the tert-butanol/water is distilled from the reaction mixture as an azeotrope. This azeotrope may subsequently be reused in subsequent preparations. The triazolinone will precipitate from the remaining water, and may then be collected by filtration. If desired, removal of residual water may be effected directly by heating under atmospheric or reduced pressure, or by the addition of heptane and removal of the heptane/water azeotrope by heating under either atmospheric or reduced pressure.

The tert-butanol medium used in this invention may be anhydrous or may contain water. The amount of tert-butanol medium and the tert-butanol/water ratio should be such that the reactants are at least partially solubilized. The amounts of tert-butanol medium used and tert-butanol/water ratios may profitably be varied depending on a variety of criteria including product yields, waste disposal considerations, specific reactants, type of production facilities, and material costs. Preferably the above reactions are carried out in a reaction medium which contains between about 50 and 1000 grams of tert-butanol for each mole of the primary reactant, the hydrazine, hydrazone, or triazolidinone. The weight of water initially making up the reaction medium is less than the weight of tert-butanol in the reaction medium. Preferably the tert-butanol medium introduced into the reaction system is between 95/5 and 70/30 tert-butanol/water. In the preferred mode an 88/12 tert-butanol medium is introduced into the system, being the azeotrope recycled from a previous production run. It is recognized that at the start of, or during a production run, the recycled tert-butanol/water azeotrope may be supplemented with additional water, tert-butanol or tert-butanol/water medium to replenish the medium, to improve process operation, to better solubilize reagents, or for other purposes. The medium composition may thereby change and may contain recycled tert-butyl azeotrope as well as other components.

The above process is preferably conducted at atmospheric pressure, although this is not critical provided that the reaction temperature is suitably varied with pressure.

In the above process steps, the reaction medium is preferably subjected to at least mild agitation, such as stirring.

The invention may be practiced as a large scale batch process producing up to and greater than 100 pound-moles of product utilizing a similar amount starting material. In a preferred mode, the production of the aryl triazolinone from the aryl hydrazone or aryl hydrazine is conducted in a single reactor with the sequential addition of the individual reactants without the isolation of the intermediate products. However, the phenylhydrazone or triazolidinone may be produced externally and then used as a starting material in the following step of the process.

The preferred mode is a batch process yielding between about 1 and 20 lb-moles of a phenyltriazolinone, and utilizing a similar molar amount of phenyl hydrazine starting material.

Economics favor large scale production if high yields can be obtained. Pilot plant triazolinone production in a 500 gallon reactor using a tert-butanol medium has given yields of 88.6% (Example 6). This compares with large scale (50 and 500 gallon reactors) production using an acetic acid medium in which a maximum yield of 64% was obtained (Example 8).

The invention may be practiced using commercially available starting materials or those which may be prepared by techniques described in the literature or modifications thereof which are known in the art. The following Examples are given to illustrate this invention further.

EXAMPLE 1

PREPARATION OF 4,5-DIHYDRO-3-METHYL-1-PHENYL-1,2,4-TRIAZOL-5(1H)-ONE

A stirred solution of 54.4 grams (0.500 mole) of phenylhydrazine in 150 grams of tert-butanol/water (88/12) was cooled to 0° to 5° C., and a solution of 23.1 grams (0.525 mole) of acetaldehyde in 50 grams of tert-butanol/water (88/12) was added dropwise during a 20 minute period. The addition caused the reaction mixture temperature to rise to 8° C. Upon completion of addition, the reaction mixture was stirred for five minutes, and a slurry of 39.8 grams (91.5% pure, 0.560 mole) of sodium cyanate in 90 grams of water was added in one portion. The addition caused the reaction mixture temperature to rise to 12° C. Additional water, 27 grams, was used to wash any of the remaining slurry of sodium cyanate from its container into the reaction mixture. Upon completion of addition, the reaction mixture was cooled to 0° to 5° C., and 39.3 grams (0.655 mole—5% equivalent excess, based on equivalents of sodium cyanate and its sodium carbonate impurity) of acetic acid was added dropwise during a 15 minute period. Upon completion of addition, the reaction mixture was stirred for about two hours during which time it was allowed to warm to about 20° C.

During the two hour stirring time a 12.4% (wt/wt) aqueous solution of sodium hypochlorite was prepared. This preparation was accomplished by bubbling 41.8 grams (0.590 mole) of chlorine gas through tubing connected to the stem of a funnel, which was inverted beneath the surface of a stirred solution of 48.3 grams (1.210 mole) of sodium hydroxide in 261.9 grams of ice/water.

Upon completion of the two-hour stirring time, the reaction mixture was cooled to about 10° C. and 321 grams (0.537 mole) of the 12.4% solution of sodium hypochlorite was added dropwise during a 40 minute period. Upon completion of addition, the reaction mixture was stirred for an additional 40 minutes and then was allowed to stand for about 18 hours during which time it warmed to ambient temperature. The tert-butanol medium was then distilled from the reaction mixture by slowly heating the stirred reaction mixture to about 100° C. Upon completion of the distillation, the solidified pot residue was collected by filtration and washed with 500 ml of water. The solid was dried, yielding 82.5 grams of 4,5-dihydro-3-methyl-1-phenyl-1,2,4-triazol-5(1H)-one (93.1% yield). Gas chromatographic analysis of the product indicated it to be 98.9% pure.

EXAMPLE 2

PREPARATION OF 1-(4-CHLOROPHENYL)-4,5-DIHYDRO-3-METHYL-1,2,4-TRIAZOL-5(1H)-ONE

A stirring solution of 71.3 grams (0.500 mole) of 4-chlorophenylhydrazine in 175 ml of tert-butanol/water (88/12) is cooled to 0° to 5° C. and a solution of 23.4 grams (0.525 mole) of acetaldehyde in 50 grams of tert-butanol/water (88/12) is added dropwise during a 20 minute period. Upon completion of addition, the reaction mixture is stirred for five minutes, and a slurry of 39.8 grams (91.5% pure—0.560 mole—12% molar excess) of sodium cyanate in 90 grams of water is added in one portion. Additional water is used to wash any of the remaining slurry of sodium cyanate from its container into the reaction mixture. The reaction mixture is cooled to 0° to 5° C., and 39.3 grams (0.655 mole—5% equivalent excess, based on equivalents of sodium cyanate and its sodium carbonate impurity) of acetic acid is added dropwise during a 15 minute period. Upon completion of addition, the reaction mixture is stirred for about two hours during which time it is allowed to warm to about 20° C. Upon completion of the two hour stirring time, the reaction mixture is cooled to 10° C., and 321 grams (0.537 mole) of a 12.4% aqueous solution of sodium hypochlorite is added dropwise during a 40 minute period. Upon completion of addition, the reaction mixture is stirred for an additional 40 minutes. The tert-butanol/water medium is then distilled from the reaction mixture by slowly heating the reaction mixture to about 100° C. Upon completion of the distillation, the pot residue is filtered, washed with water and dried, yielding 1-(4-chlorophenyl)-4,5-dihydro-3-methyl-1,2,4-triazol-5(1H)-one.

EXAMPLE 3

PREPARATION OF 1-(4-CHLORO-2-FLUOROPHENYL)-4,5-DIHYDRO-3-METHYL-1,2,4-TRIAZOL-5(1H)-ONE

A stirring solution of 80.3 grams (0.500 mole) of 4-chloro-2-fluorophenylhydrazine in 180 ml of tert-butanol/water (88/12) is cooled to 0° to 5° C., and a solution of 23.4 grams (0.525 mole) of acetaldehyde in 50 grams of tert-butanol/water (88/12) is added dropwise during a 20 minute period. Upon completion of addition, the reaction mixture is stirred for five minutes, and a slurry of 39.8 grams (91.5% pure—0.560 mole—12% molar excess) of sodium cyanate in 90 grams of water is added in one portion. Additional water is used to wash any of the remaining slurry of sodium cyanate from its container into the reaction mixture. The reaction mixture is cooled to 0° to 5° C. and 39.3 grams (0.655 mole—5% equivalent excess, based on equivalents of sodium cyanate and its sodium carbonate impurity) of acetic acid is added dropwise during a 15 minute period. Upon completion of addition, the reaction mixture is stirred for about two hours during which time it is allowed to warm to about 20° C. Upon completion of the two hour stirring time, the reaction mixture is cooled to 10° C. and 321 grams (0.537 mole) of a 12.4% aqueous solution of sodium hypochlorite is added dropwise during a 40 minute period. Upon completion of addition, the reaction mixture is stirred for an additional 40 minutes. The tert-butanol/water medium is then distilled from the reaction mixture by slowly heating the reaction mixture to about 100° C. Upon completion of the distillation, the pot residue is filtered, washed with water and dried, yielding 1-(4-chloro-2-fluorophenyl)-4,5-dihydro-3-methyl-1,2,4-triazol-5(1H)-one.

EXAMPLE 4

PREPARATION OF 1-(2,4-DICHLORO-5-METHYLSULFONYLAMINOPHENYL)-4,5-DIHYDRO-3-METHYL-1,2,4-TRIAZOL-5(1H)-ONE

A stirring solution of 117.3 grams (0.500 mole) of (2,4-dichloro-5-(methylsulfonylamino)phenylhydrazine in 200 ml of tert-butanol/water (88/12) is cooled to 0° to 5° C. and a solution of 23.4 grams (0.525 mole—5% excess) of acetaldehyde in 50 grams of tert-butanol/water (88/12) is added dropwise during a 20 minute period. Upon completion of addition, the reaction mixture is stirred for five minutes, and a slurry of 39.8 grams (91.5% pure—0.560 mole—12% molar excess) of sodium cyanate in 90 grams of water is added in one portion. Additional water is used to wash any of the remaining slurry of sodium cyanate from its container into the reaction mixture. The reaction mixture is cooled to 0° to 5° C., and 39.3 grams (0.655 mole—5% equivalent excess, based on equivalents of sodium cyanate and its sodium carbonate impurity) of acetic acid is added dropwise during a 15 minute period. Upon completion of addition, the reaction mixture is stirred for about two hours during which time it is allowed to warm to about 20° C. Upon completion of the two hour stirring time, the reaction mixture is cooled to 10° C. and 321 grams (0.537 mole) of a 12.4% aqueous solution of sodium hypochlorite is added dropwise during a 40 minute period. Upon completion of addition, the reaction mixture is stirred for an additional 40 minutes. The tert-butanol/water medium is then distilled from the reaction mixture by slowly heating the reaction mixture to about 100° C. Upon completion of the distillation, the pot residue is filtered, washed with water and dried, yielding 1-(2,4-dichloro-5-methylsulfonylaminophenyl)-4,5-dihydro-3-methyl-1,2,4-triazol-5(1H)-one.

EXAMPLE 5

PREPARATION OF 4,5-DIHYDRO-3-METHYL-1-PHENYL-1,2,4-TRIAZOL-5(1H)-ONE

A fifty gallon reactor was charged with 61.1 pounds of tert-butanol/water (88/12) which was stirred and cooled to 5° C. To this was added 22.0 pounds (0.203 lb-mole) of phenylhydrazine. While maintaining the temperature of the reaction mixture at 0° to 5° C., a solution of 9.3 pounds (0.211 lb-mole) of acetaldehyde in 20 pounds of tert-butanol/water (88/12) was added during a 90 minute period. After this time a mixture of 15.6 pounds (0.240 lb-mole) of 85% pure sodium cyanate in 44.5 pounds of water was added during a five-minute period. The addition caused the temperature of the reaction mixture to rise about 5° to 10° C. The reaction mixture was again cooled to 5° C. as it was stirred during a 30 minute period. While maintaining the reaction mixture at about 10° C., 14.8 pounds (0.247 lb-mole) of acetic acid was added during about a 30–45 minute period. Upon completion of the addition, the reaction mixture was stirred for three hours at about 10° C. until the reaction was complete. The reaction endpoint and the concentration of the phenyltriazolidinone intermediate was determined by gas chromatography. Upon completion of the reaction, a solution of 12.6 pounds of sodium chloride in 35.8 pounds of water was stirred into the reaction mixture. The aqueous phase was separated when the temperature of the reaction mixture was about 15° C. While maintaining the temperature of the reaction mixture at 20° C. 120.5 pounds of aqueous 11.1% (wt/wt) sodium hypochlorite (0.180 lb-mole) was added to the reaction mixture during a three-hour period. Upon completion of addition, the reaction mixture, was stirred for one hour at 20° C. After this time, 67.8 pounds of water was added to the reaction mixture and 73.4 pounds of tert-butanol/water (88/12) was removed by distillation at an overhead temperature of 80° C. The residue was cooled to 0° C., and a solid was collected by filtration. The solid was dried at 80° C./5 mm Hg for 24 hours, yielding 32.2 pounds (91% yield) of 4,5-dihydro-3-methyl-1-phenyl-1,2,4-triazol-5(1H)-one.

EXAMPLE 6

PREPARATION OF 4,5-DIHYDRO-3-METHYL-1-PHENYL-1,2,4-TRIAZOL-5(1H)-ONE

A 500 gallon reactor was charged with 71.5 pounds of water and 534 pounds of (88/12) tert-butanol/water medium which was stirred and cooled to 5° C. To this was added 220 pounds (2.03 lb-mole) of phenylhydrazine. While maintaining the reaction mixture temperature at about 0° C. to 9° C., a solution of 93 pounds (2.11 lb-moles) of acetaldehyde in 207 pounds of tert-butanol/water (88/12) was added during a 3 hour 20 minute period. At the end of this time, a mixture of 155 pounds (2.38 lb-mole) of 85% pure sodium cyanate in 991 pounds of water was added during a ten minute period. The addition caused the temperature of the reaction mixture to rise to about 14° C. The reaction mixture was then cooled to about 8° C. as it was stirred over a 50 minute period. While maintaining the reaction mixture temperature at about 6° C. to 12° C., 148 pounds (2.47 lb-mole) of acetic acid was added during about a 95 minute period. Upon completion of addition, the reaction mixture was stirred for 3 hours at about 10°

C. until the reaction was complete. The progress of the reaction was monitored by thin layer chromatography. After this time, a solution of 125.8 pounds of sodium chloride in 358 pounds of water was stirred into the reaction mixture during a 30 minute period. Upon completion of addition, the reaction mixture was allowed to stand for one hour to allow separation of the aqueous phase. After this time the aqueous phase was removed from the reaction mixture. The reaction mixture was cooled to about 7° C., and 1234.3 pounds of 11.2% (wt/wt) aqueous sodium hypochlorite (1.86 lb-mole) was added to the reaction mixture over about an eight hour period. During this time, the reaction mixture temperature rose to about 13° C. Upon completion of addition, the reaction mixture was stirred for one hour after which 678 pounds of water was added. The mixture was heated to about 102° C., and 667 pounds of tert-butanol/water (88/12) was removed by distillation at an overhead temperature of about 80° C. The residue was stirred with 50 pounds of water and cooled to about 0° C. The solid was collected by centrifugation, yielding 342.0 pounds of wet product which on the basis of a dried analyzed sample, contained 318.5 pounds (88.6% yield) of 4,5-dihydro-3-methyl-1-phenyl-1,2,4-triazol-5(1H)-one (98.9% purity).

EXAMPLE 7

PREPARATION OF
3-METHYL-1-PHENYL-1,2,4-TRIAZOLIDIN-5-ONE

A 500 gallon reactor is charged with 61.1 pounds of tert-butanol (88/12 azeotrope with water) which is stirred and cooled to 5° C. To this is added 22.0 pounds (0.203 lb-mole) of acetaldehyde phenylhydrazone. While maintaining the temperature of the reaction mixture at 0° to 5° C., 15.6 pounds (0.240 lb-mole) of 85% pure sodium cyanate in 44.5 pounds of water is added during a five-minute period. The reaction mixture is maintained at 5° C. as it is stirred during a 30 minute period. While maintaining the reaction mixture at about 10° C., 14.8 pounds (0.247 lb-mole) of acetic acid is added during about a 30–45 minute period. Upon completion of the addition, the reaction mixture is stirred for three hours at about 10° C. until the reaction is complete. The reaction endpoint and the concentration of the phenyltriazolidinone intermediate are determined by gas chromatograph. At the end of this time, a solution of 12.6 pounds of sodium chloride in 35.8 pounds of water is stirred into the reaction mixture. The aqueous phase is separated when the reaction mixture temperature is about 15° C. After this time, 67.8 pounds of water is added to the reaction mixture and 73.4 pounds of tert-butanol/water (88/12) is removed by distillation at an overhead temperature of 80° C. The residue is cooled to 0° C., and a solid is collected by filtration. The solid is dried at 80° C./5 mm Hg for 24 hours to yield 3-methyl-1-phenyl-1,2,4-triazolidin-5-one.

EXAMPLE 8

PREPARATION OF
4,5-DIHYDRO-3-METHYL-1-PHENYL-1,2,4-TRIAZOL-5(1H)-ONE USING ACETIC ACID AS SOLVENT

In a 50 gallon reactor, a stirred solution of 12 pounds (0.111 lb mole) of phenylhydrazine in 115 pounds of glacial acetic acid was cooled to about 5° to 10° C., and a solution of 5.2 pounds (0.087 lb mole) of acetaldehyde in 6.1 pounds of acetic acid was added at a rate that maintained the reaction mixture temperature at about 12° to 15° C. The complete addition required about five minutes. Immediately upon completion of addition, a cold solution (about 15° C.) of 7.6 pounds (0.117 lb mole) of sodium cyanate in 72 pounds of water was added at a rate that maintained the reaction mixture temperature at about 8° to 12° C. The complete addition required about 30 minutes. Upon completion of addition, the reaction mixture was stirred for 20 minutes and then was warmed to about 20° C. A solution of 13.3 pounds (0.179 lb mole) of sodium hypochlorite in 119.7 pounds of water was then added at a rate that maintained the reaction mixture temperature at 25° to 40° C. The complete addition required about one hour. Upon completion of addition, the reaction mixture was stirred for about one hour, and then about 220 pounds (approximately 72%) of the acetic acid/water solvent was removed by distillation under vacuum (50 mm Hg). Water, 82 pounds, was added, and the resultant slurry was cooled to 25° C. The product was isolated by centrifugation and washed on the centrifuge with water. The product was dried at 70° C. under vacuum, yielding 14.8 pounds of 84.4% pure 4,5-dihydro-3-methyl-1-phenyl-1,2,4-triazol-5(1H)-one (64.2% yield).

What is claimed is:

1. A process for the production of an aryl triazolinone of the formula

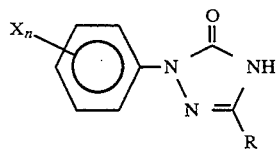

wherein
R is lower alkyl and
$X_n$ is 2,4-dichloro-5-methylsulfonylamino; 2-chloro-5-methylsulfonylamino; 4-chloro-5-methylsulfonylamino; 3-methylsulfonylamino; 4-chloro; 2-chloro; 3-nitro; 4-chloro-3-nitro; 2-chloro-5-nitro; 2,4,dichloro-5-nitro;2-fluoro; 2-fluoro-4-chloro; 2,4-dichloro; 4-alkoxy; or 4-alkoxy-2-fluoro;
which comprises:
a) reacting an aryl hydrazine of the formula

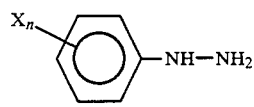

in a tert-butanol medium with an aldehyde of the formula R—C(O)H to produce the aryl hydrazone of formula;

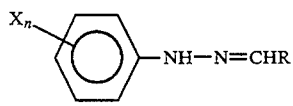

b) treating the aryl hydrazone so produced in a tert-butanol medium with an alkali metal cyanate, in the presence of an organic acid to produce an aryl triazolidinone of the formula

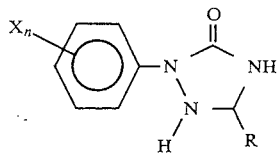

c) treating the aryl triazolidinone so produced with a hypohalous acid or a salt thereof, or a halogen of the group consisting of chlorine, bromine, and iodine to produce the aryl triazolinone.

2. The process of claim 1 in which R is methyl.

3. The process of claim 1 which is a batch process in which between 1 lb-mole and 100 lb-moles of triazolinone are produced.

4. The process of claim 1 in which the tert-butanol medium contains tert-butanol/water azeotrope recycled from a previous production run.

5. The process of claim 1 which is conducted without isolating either the aryl hydrazone or the triazolidinone from the tert-butanol reaction medium.

6. The process of claim 1 in which the tert-butanol medium contains 88 per cent by weight tert-butanol and 12 percent by weight water.

7. The process of claim 1 in which $X_n$ is 2-fluoro.

8. The process of claim 1 in which $X_n$ is 2-fluoro-4-chloro.

9. The process of claim 1 in which $X_n$ is 4-chloro.

10. The process of claim 1 in which $X_n$ is 2,4-dichloro.

11. The process of claim 1 in which the acid is acetic acid.

* * * * *